(12) United States Patent
Pommereau et al.

(10) Patent No.: US 10,874,801 B2
(45) Date of Patent: Dec. 29, 2020

(54) SYSTEM COMPRISING A DRUG DELIVERY DEVICE AND A CARTRIDGE PROVIDED WITH A BUNG AND A METHOD OF IDENTIFYING THE CARTRIDGE

(71) Applicant: Sanofi-Aventis Deutschland GmbH, Frankfurt am Main (DE)

(72) Inventors: Christian Pommereau, Frankfurt am Main (DE); Anke Liewald, Frankfurt am Main (DE); Michael Jugl, Frankfurt am Main (DE); Axel Teucher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 15/489,497

(22) Filed: Apr. 17, 2017

(65) Prior Publication Data
US 2017/0216528 A1 Aug. 3, 2017

Related U.S. Application Data

(63) Continuation of application No. 13/321,483, filed as application No. PCT/EP2010/056989 on May 20, 2010, now Pat. No. 9,855,389.

(30) Foreign Application Priority Data

May 20, 2009 (EP) .................................. 09006819
Sep. 18, 2009 (EP) .................................. 09170686

(51) Int. Cl.
*A61M 5/315* (2006.01)
*A61M 5/24* (2006.01)
(Continued)

(52) U.S. Cl.
CPC ............ *A61M 5/31511* (2013.01); *A61J 1/06* (2013.01); *A61J 1/065* (2013.01); *A61M 5/2422* (2013.01);
(Continued)

(58) Field of Classification Search
CPC .......... A61M 5/31511; A61M 2205/60; A61M 2205/6027; A61M 2205/6054;
(Continued)

(56) References Cited

U.S. PATENT DOCUMENTS 533,575 A 2/1895 Wilkens
2,607,342 A 8/1958 Abel
(Continued)

FOREIGN PATENT DOCUMENTS

DE 10051575 A1 2/2002
DE 10226643 A1 1/2004
(Continued)

OTHER PUBLICATIONS

Definition "embedded" from Merriam-Webster Dictionary [Online] Retrieved from May 31, 2109. (Year: 2019).*
(Continued)

*Primary Examiner* — Jenna Zhang
(74) *Attorney, Agent, or Firm* — McCarter & English, LLP (57) ABSTRACT

A system comprising a drug delivery device and a cartridge provided with a bung and and a method of identifying the cartridge The present invention relates to a bung (20), to a drug containing cartridge (10) and to a drug delivery device, wherein the bung (20) comprises a coding feature (28) for carrying information regarding at least one of the cartridge
(Continued)

(10) and the content of the cartridge (10). Furthermore, it relates to a method for identifying a cartridge (10) containing a medicinal product.

21 Claims, 4 Drawing Sheets (51) Int. Cl.
*A61J 1/06* (2006.01)
*A61M 5/28* (2006.01)
*A61M 5/50* (2006.01)

(52) U.S. Cl.
CPC .......... *A61M 5/28* (2013.01); *A61M 5/31515* (2013.01); *A61M 5/24* (2013.01); *A61M 5/5086* (2013.01); *A61M 2205/3368* (2013.01); *A61M 2205/60* (2013.01); *A61M 2205/6027* (2013.01); *A61M 2205/6045* (2013.01); *A61M 2205/6054* (2013.01); *A61M 2205/6081* (2013.01)

(58) Field of Classification Search
CPC .............. A61M 2205/6063–2205/6081; A61M 5/24–5/288; A61J 1/06; A61J 1/062; A61J 1/065
See application file for complete search history.

(56) References Cited

U.S. PATENT DOCUMENTS

| | | | |
|---|---|---|---|
| 4,501,192 A | 2/1985 | Knödel | |
| 4,543,093 A | 9/1985 | Christinger | |
| 4,766,980 A | 8/1988 | Engle | |
| 5,226,895 A | 7/1993 | Harris | |
| 5,279,586 A | 1/1994 | Balkwill | |
| 5,290,228 A * | 3/1994 | Uemura | A61M 5/19 604/220 |
| 5,300,031 A * | 4/1994 | Neer | A61M 5/14546 128/DIG. 1 |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,607,400 A | 3/1997 | Thibault et al. | |
| 5,626,566 A | 5/1997 | Petersen et al. | |
| 5,674,204 A | 10/1997 | Chanoch | |
| 5,688,251 A | 11/1997 | Chanoch | |
| 5,808,203 A * | 9/1998 | Nolan, Jr. | A61M 5/14546 604/67 |
| 5,865,798 A | 2/1999 | Grimard et al. | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,652,489 B2 * | 11/2003 | Trocki | A61M 5/14546 600/432 |
| 6,899,698 B2 | 5/2005 | Sams | |
| 6,936,032 B1 | 8/2005 | Bush, Jr. et al. | |
| 7,018,363 B2 | 3/2006 | Cowan et al. | |
| 7,195,609 B2 | 3/2007 | Huegli | |
| 7,241,278 B2 | 7/2007 | Moller | |
| 7,419,478 B1 | 9/2008 | Reilly et al. | |
| 7,588,186 B2 | 9/2009 | Steffen et al. | |
| 7,682,345 B2 | 3/2010 | Savage | |
| 9,415,169 B2 | 8/2016 | Tachikawa et al. | |
| 9,623,191 B2 * | 4/2017 | Uber, III | A61M 5/31573 |
| 9,636,452 B2 * | 5/2017 | Trocki | A61M 5/14546 |
| 2001/0034506 A1 * | 10/2001 | Hirschman | A61M 5/14546 604/207 |
| 2002/0052578 A1 | 5/2002 | Moller | |
| 2002/0120235 A1 | 8/2002 | Enggaard | |
| 2003/0050609 A1 | 3/2003 | Sams | |
| 2003/0078195 A1 | 4/2003 | Kristensen et al. | |
| 2003/0125670 A1 | 7/2003 | Langley et al. | |
| 2003/0233075 A1 * | 12/2003 | Huegli | A61M 5/31513 604/222 |
| 2004/0059299 A1 | 3/2004 | Moller | |
| 2004/0133162 A1 * | 7/2004 | Trocki | A61M 5/14546 604/131 |
| 2004/0178255 A1 | 9/2004 | Eich et al. | |
| 2004/0186437 A1 * | 9/2004 | Frenette | A61M 5/31511 604/189 |
| 2004/0210199 A1 | 10/2004 | Atterbury et al. | |
| 2004/0267207 A1 | 12/2004 | Veasey et al. | |
| 2005/0101920 A1 | 5/2005 | Keane et al. | |
| 2005/0113765 A1 | 5/2005 | Veasey et al. | |
| 2005/0197626 A1 | 9/2005 | Moberg et al. | |
| 2006/0153693 A1 | 7/2006 | Fiechter et al. | |
| 2007/0219503 A1 | 9/2007 | Loop et al. | |
| 2007/0219507 A1 * | 9/2007 | Dai | A61M 5/31511 604/218 |
| 2007/0219508 A1 | 9/2007 | Bisegna et al. | |
| 2007/0257111 A1 | 11/2007 | Ortenzi | |
| 2008/0183122 A1 * | 7/2008 | Fisher | G01N 21/31 604/21 |
| 2008/0308580 A1 * | 12/2008 | Gaydos | A61M 5/14566 222/333 |
| 2009/0247867 A1 | 10/2009 | Spohn et al. | |
| 2009/0275916 A1 | 11/2009 | Harms et al. | |
| 2010/0262002 A1 | 10/2010 | Martz | |
| 2011/0240747 A1 * | 10/2011 | Stewart | F16J 15/064 235/492 |
| 2011/0264033 A1 * | 10/2011 | Jensen | A61M 5/486 604/65 |
| 2012/0143147 A1 * | 6/2012 | Pommereau | A61M 5/31511 604/218 |

FOREIGN PATENT DOCUMENTS

| | | |
|---|---|---|
| EP | 0743072 A2 | 11/1996 |
| EP | 0879611 A2 | 11/1998 |
| EP | 0893133 A1 | 1/1999 |
| EP | 0937471 A2 | 8/1999 |
| EP | 0937476 A2 | 8/1999 |
| EP | 2407195 A1 | 1/2012 |
| GB | 391177 | 4/1933 |
| GB | 578827 | 7/1946 |
| JP | 2007531181 A | 11/2007 |
| RU | 2062165 C1 | 6/1996 |
| WO | 1901111 A1 | 12/1979 |
| WO | 9938554 A1 | 8/1999 |
| WO | 0110484 A1 | 2/2001 |
| WO | 0156635 A1 | 8/2001 |
| WO | 03017915 A1 | 3/2003 |
| WO | 2004084795 A1 | 10/2004 |
| WO | 2005099793 A1 | 10/2005 |
| WO | 2008038896 A1 | 4/2008 |
| WO | 2008113772 A1 | 9/2008 |
| WO | 2009024562 A1 | 2/2009 |
| WO | 2010103919 A1 | 9/2010 |
| WO | 2010133675 A1 | 11/2010 |
| WO | 2010133676 A1 | 11/2010 |
| WO | 2011026932 A1 | 3/2011 |

OTHER PUBLICATIONS

Definition "encased" from Merriam-Webster Dictionary [Online] Retrieved from May 31, 2109. (Year: 2019).*
Communication Pursuant to Article 94(3) EPC issued in European Patent Application No. 10723073.2 dated Feb. 5, 2016.

(56) References Cited

OTHER PUBLICATIONS

Communication issued in European Patent Application No. 17152293.1 dated Jun. 12, 2017.

* cited by examiner

SYSTEM COMPRISING A DRUG DELIVERY DEVICE AND A CARTRIDGE PROVIDED WITH A BUNG AND A METHOD OF IDENTIFYING THE CARTRIDGE

CROSS REFERENCE TO RELATED APPLICATIONS

The present application is a continuation of U.S. patent application Ser. No. 13/321,483 filed Feb. 23, 2012, which is a 35 U.S.C. 371 National Application of PCT/EP2010/056979 filed May 20, 2010, which claims priority to European Patent Application No. 090006819.8 filed May 20, 2009, and European Patent Application No. 09170686.1 filed Sep. 18, 2009, the entire contents of which are incorporated entirely herein by reference.

A system comprising a drug delivery device and a cartridge provided with a bung and a method of identifying the cartridge The present invention relates to a bung for drug containing cartridges in drug delivery devices. Furthermore it relates to a cartridge and a drug delivery device comprising a bung and to a method for identifying a cartridge containing a medicinal product.

Drug delivery devices are generally known for the administration of a drug, for example insulin, but also for other fluid medicinal products. These devices are very comfortable in usage for self-administration of insulin by a patient. Because of this self-administration it is necessary to have a high dose accuracy and high security against accidentally inserting a cartridge into the drug delivery device containing the wrong medicinal product.

Some attempts to reduce this risk for the patient are described in DE 10051575 A1 and in WO 2004/084795 A1.

It is an object of the invention to provide a system comprising a drug delivery device and a cartridge provided with a bung which facilitates a selection of the cartridge, and a method of identifying a cartridge.

This object is achieved with the system according to claim 1 and with the method according to claim 15. Variations and embodiments derive from the dependent claims. The system comprises a cartridge provided with a bung. The bung comprises a first mechanical coding feature for carrying information regarding at least one of the cartridge and the content of the cartridge. The system further comprises a drug delivery device. A second mechanical coding feature is arranged in the drug delivery device. The cartridge is only mountable to the drug delivery device in case that the first and the second mechanical coding features match.

In an embodiment of the system, the bung is adapted to identify a medicinal product contained in a cartridge within a batch of medicinal products contained in other cartridges by means of the coding feature.

In a further embodiment of the system, a medicinal product can be identified by means of the visible structure of the mechanical coding feature.

In a further embodiment of the system, the bung comprises at least two different materials.

In a further embodiment of the system, the bung is moveable along a longitudinal axis of the cartridge.

In a further embodiment of the system, the first mechanical coding feature comprises a protruding ring, and the second mechanical coding feature comprises a trench.

In a further embodiment of the system, the cartridge is identifiable and/or distinguishable by the radius of the protruding ring.

In a further embodiment of the system, the first mechanical coding feature comprises a plurality of relief structures, and the second mechanical coding feature comprises a plurality of depressions.

In further embodiments of the system, a cartridge is identifiable and/or distinguishable by the shape of the relief structures and/or by the arrangement of the relief structures.

In a further embodiment of the system, the relief structures have an elongated shape with a length, and the relief structures are arranged at a distance from one another.

In a further embodiment of the system, a cartridge is identifiable and/or distinguishable by the number of the relief structures and/or by the minimal distance between the relief structures and/or by the length of the relief structures.

In a further embodiment of the system, the relief structures have an elongated shape and are arranged on a circle and parallel to a radius of the circle.

In a further embodiment of the system, the relief structures have an elongated shape and are arranged on a circle and transverse to a radius of the circle.

In a further embodiment of the system, the first mechanical coding feature is adapted to facilitate a separation of the bungs in a bulk storage.

In a method of identifying a cartridge containing a medicinal product for use in a drug delivery device, the cartridge is provided with a bung carrying a first mechanical coding feature that corresponds to a type of the cartridge or to a content of the cartridge. The coding feature is personally or automatically recognized to identify the cartridge. The cartridge may be identified visually by the structure of the coding feature. Further, the coding feature may be provided for being recognized, especially read, automatically. The cartridge may be identified by fitting it to a second mechanical coding feature that is arranged in a drug delivery device.

According to a further aspect of the present invention, a bung is provided that comprises a coding feature for carrying information regarding at least one of the cartridge and the content of the cartridge.

Assembling a coding feature in a bung and using the bung in a cartridge allows the user of a drug delivery device to enhance protection against accidentally mixing-up cartridges, which are containing different types of medicinal products. The coding feature may carry object-specific data like for example the date of production, the type of liquid medicinal product that is contained in the cartridge, the batch number, the expiry date of the contained medicinal product, the storage temperature or the production site.

In a preferred embodiment, a bung is provided which is adapted to identify a medicinal product contained in a cartridge within a batch of other medicinal products contained in cartridges by means of the coding feature.

When there are a lot of cartridges present which are not distinguishable by optical characteristics but are containing different medicinal products, it is necessary for the user to identify the right cartridge, which is containing the medicinal product the user needs. The specific element that is intended to make the cartridges and therefore their content distinguishable from other cartridges and their contents is the bung comprising a coding feature.

By means of the coding feature medicinal product counterfeiting and drug delivery device counterfeiting can be avoided and detected. The coding feature guaranties the originality of the cartridge by carrying for example the factory-number or having other characteristics that allow drawing conclusions regarding at least one of the manufacturer of the cartridge and the content of the cartridge.

In another embodiment the coding feature comprises an electronic coding feature.

One advantage of having an electronic coding feature is that a lot of different object-specific data can be carried.

The electronic coding feature may comprise an integrated circuit, an RFID-member or a solid state memory. An RFID-member comprises at least an antenna and an integrated circuit like for example a microchip.

According to another preferred embodiment, the electronic coding feature is located at the surface of the bung.

Depending on the type of electronic coding feature it could be advantageous to locate the electronic coding feature on a surface of the bung. Some methods of interaction with the electronic coding feature need a direct contact with the electronic coding feature.

This is for example caused by the range of a sensing device. Some sensing devices and the corresponding electronic coding features have only a very short range. If the distance between the electronic coding feature and the sensing device is beyond this range the sensing device can not interact with the electronic coding feature.

Some electronic coding features need a current supply. In case that the electronic coding feature is located at the surface of the bung a contact to a current supply can easily be made.

One advantage of locating the electronic coding feature at the surface of the bung could be that the electronic coding feature made use of can be attached more easily to the surface of the bung.

In another preferred embodiment, the electronic coding feature is located inside the bung (e.g., fully encased within the bung).

An electronic coding feature inside the bung is not as easy to dislocate or to remove as an electronic coding feature positioned at the surface.

Some methods to interact with an electronic coding feature are particularly sensitive to the position of the electronic coding feature in relation to the sensing device.

In case of a dislocation the electronic coding feature is no longer in an appropriate position and possible interaction with a sensing device might be impeded.

If one removed the electronic coding feature, the content of the cartridge could no longer be sealed if the bung is destroyed due to the removal of the electronic coding feature. Therefore, the cartridge is no longer usable. Additionally, the content of the cartridge and the origin of the cartridges themselves which are manufactured in in-house production can not be detected.

According to another preferred embodiment, the electronic coding feature comprises a transponder.

A transponder contains a code which can be read out. Active as well as passive transponders are possible to be used. The two types of transponders differ in the current supply. A passive transponder needs energy supply for operating. By means of an electromagnetic wave sent from a sensing device signal transmission is initiated. This electromagnetic wave serves as energy supply for the passive transponder.

An active transponder comprises separate means for its energy supply like for example a battery.

Furthermore, active transponders can comprise integrated sensors 31.

One example for a cheap transponder is a RFID-member which is used with an external reader, also known as transceiver. The reader is sending a signal whereon the RFID-member is responding and the reader is receiving the answer from the RFID-member. This received answer can be transmitted to a computer system. The data can be compared to a database to gain more object-specific data.

Using an RFID-member has the advantage that RFID-members are not limited to a single type of code for a particular product. A RFID-member has a larger capacity, at least large enough to carry a unique code for each individual bung.

In a particularly preferred embodiment, the electronic coding feature is writeable.

Read-write-transponder use technologies to store date like for example EEPROM, FRAM or SRAM. The main difference between these technologies is that the latter is volatile and the first two are non-volatile.

According to another preferred embodiment, the electronic coding feature can be read out.

To read-out for example the code of a transponder, the transmitting and receiving antenna of a sensing device sets up an electromagnetic field in an area where the transponder is located. This electromagnetic field has a specific frequency. The transponder answers to this electromagnetic field by sending a code prompted by the electromagnetic field. This code is sensed by the antenna of the sensing device and is compared with stored data.

In another preferred embodiment the bung comprises at least two different materials.

A first material is covering at least the whole lateral area of the bung. This first material comprises a relatively high compressibility. Due to the high compressibility of the first material, the bung is able to adapt its shape to the shape of the main body portion of the cartridge. Furthermore it is preferred that the first material is chosen in a way that the bung is enabled to be easily slided by a piston in axial direction along the main body portion. The bung is driven forward by mechanical contact between the piston and the bung.

Materials that may be considered for coating the surface are, for example, silicone rubber and acrylic rubber. All elastomers are conceivable for being used as first material.

The surface material should almost completely resist being dissolved in the drug contained in the cartridge and particularly, if the surface material is a polymer very few monomers should be dissolved. There should also be only low abrasion with the cartridge while the bung is axially displaced for dispensing the drug.

The second material is at least partly arranged inside the bung and provides a rigid or semi-rigid core to resist or at least to limit axial compression of the bung while a piston is pressed onto the bung and is applying a force in distal direction. The second material can comprise for example glass, metal, ceramic, rubber, plastic or gel.

A way to manufacture such a bung is by injection molding. One advantage of injection molding is that hard/soft material combinations can be processed at the same time by multi-component injection molding.

There are many processes that can be used to manufacture a bung comprising at least two different materials. One example is the sandwich process. There are two melts which are successively die-casted into a cavity by means of a mixing head. The resulting structure is a core-shell structure in case that only two melts are used, or a multi-layer structure in case that more than two melts are used.

By having a thin layer coating the core of the bung the compression of the whole bung is reduced and thus the bung has also a reduced retention time after compression. This compression results from the pressure of the piston exerted on the bung while the medicinal product is dispensed from the cartridge.

Other advantages due to the special structure of the bung are a shorter retention time for keeping the needle in the skin and a reduced dripping time of the medicinal product out of the needle after injection.

By covering the distal end face and the lateral area of the bung, it is possible to have a consistent surface structure in the lateral area and at the distal end face of the bung which can be manufactured easily.

A flat surface of the bung at the distal end face is advantageous to increase the dose accuracy not only while dispensing the last dose from the medicament cartridge, wherein dose means a certain volume of a liquid medicinal product. To dispense the last dose of the drug, the bung is moved forward by means of a mechanical contact with a piston in a drug delivery device.

Near the distal end of the cartridge, an edge of the distal end face of the bung abuts a shoulder portion of the cartridge and the bung comes to a stop. While abutting this shoulder portion, the first material, in particular the first material at the edge of the distal end face, is compressed in axial direction.

By having a flat surface and a constant and thin layer thickness at the distal end face of the bung, it is possible to have a constant compression at the distal end face of the bung while abutting the shoulder portion of the cartridge. By means of the structure of the bung additional components responsible for ensuring the stop of the cartridge bung at the end of the cartridge can be eliminated.

In another preferred embodiment the bung comprises an electronic coding feature arranged inside the bung and is surrounded by an electrically isolating material.

One advantage of an electrically isolating material is to avoid a short-circuit of the electronic coding feature arranged inside the bung.

According to another preferred embodiment the electronic coding feature inside the bung is surrounded by a polymer-matrix.

In case that the first and the second material comprise a polymer, a polymer with a smaller compressibility than the first material is used as second material. The material used as second material has a longer chain length than the first material in order to decrease the compressibility. By varying the chain length of the polymer materials, the strength and toughness of the materials can be modulated. Crosslinking, like vulcanization also increases strength and toughness of the material.

By increasing the chain length, the chain interactions also increase and therefore the Van-der-Waals-attractions and entanglements increase. The chains are held in position more strongly and resist deformations. The result is that the matrix breaks up at higher stresses and higher temperatures. Besides the chain length having an influence on the properties of a polymer, there is another influence given by the fact that a polymer is branched or unbranched. Basically, the more branched a polymer is, the tighter is the polymer.

The first material can be manufactured by injection molding. After forming a shell via injection molding, monomers and the electronic coding feature are added inside this shell. One advantage of a polymer can be that the material can be liquid at low temperature and polymerize inside the shell. After the polymerization, the material can form a rigid core inside the bung and it surrounds the electronic coding feature.

According to another aspect of the present invention, a drug delivery device comprises means to interact with an electronic coding feature.

This means to interact with the electronic coding feature can be for example an electromagnetic sensing device. This sensing device can interact with the electronic coding feature to share information like for example the position of the bung inside the cartridge. This information allows drawing conclusions concerning the liquid level of the content of the cartridge. The sensing device may comprise a microcontroller and a memory which can store not only data sent from the electronic coding feature, but also data from other sensors.

In another preferred embodiment, the drug delivery device comprises a cartridge and a bung and further comprises external means arranged outside the drug delivery device being able to interact with the electronic coding feature.

External means can be used to detect a certain cartridge. For this purpose the cartridge can be arranged outside a drug delivery device to get information stored on the electronic coding feature concerning for example the storage temperature or the expiry date of the cartridge. The storage temperature is of special interest for most medicinal products.

If a medicinal product is stored at the wrong temperature it can lose its effectivity and can be the cause of severe health problems for the user. These wrongly stored cartridges can be sorted out before being arranged inside a drug delivery device via using an external means that detects defective cartridges.

Also, in case of a recall campaign, the defective cartridges can be sorted out by being detected by the external means.

According to another preferred embodiment, the means that interacts with the electronic coding feature is an electromagnetic sensing device.

This electromagnetic sensing device can be arranged inside the drug delivery device or can be part of an external means that can interact with the electronic coding feature. An electromagnetic sensing device can work as reader for RFID-members.

Another aspect of the present invention is that the bung comprises a mechanical coding feature.

The mechanical coding feature can be arranged for example at the distal end of the bung.

According to another embodiment, the bung comprises both an electronic coding feature and a mechanical coding feature.

The purpose of having a mechanical coding feature may for example be to avoid assembling accidentally a wrong cartridge to a drug delivery device.

A sensor which detects if the mechanical coding feature abuts a complementary feature in the drug delivery device may be provided. If this sensor detects that the drug delivery device does not fit to the cartridge a warning signal can be emitted that alerts the user.

In another preferred embodiment the medicinal product can be identified by means of the visible structure of the mechanical coding feature.

The mechanical coding feature can for example be colored. Every different color or pattern is characteristic for a medicinal product contained in the cartridge.

The mechanical coding feature can be distinguishable by means of the specific shape of the mechanical coding feature. The mechanical coding feature can form for example a square, a triangle or a star.

According to another aspect of the present disclosure a drug delivery device comprising a bung and a cartridge is described. A first mechanical coding feature is arranged at the bung of the cartridge and a second mechanical coding feature is arranged in the drug delivery device. The cartridge, which comprises the bung, is only mountable to the drug delivery device in case that the first and the second mechanical coding feature match.

By using a mechanical coding feature at the bung of a cartridge and a drug delivery device which is accordingly coded, a mix-up of different drugs and devices can be avoided. An audio warning can be provided in case that the cartridge and the drug delivery device do not match.

According to a preferred embodiment, the bung is moveable along a longitudinal axis of the cartridge.

While the bung is moving along the longitudinal axis of the cartridge, there can be additional sensors which are disposed to scan the surface of the main body portion of the cartridge. These sensors could for example detect glass breakage and warn the user.

According to another aspect of the present disclosure, a method to identify a cartridge containing a medicinal product is provided wherein the cartridge comprises a bung and wherein the bung is located inside the cartridge and comprises a coding feature which is carrying information regarding at least one of the cartridge and the content of the cartridge, wherein the information can be read-out or written on the coding feature by a means that is able to interact with the coding feature, wherein this information makes the cartridge and the content of the cartridge distinguishable within a batch of other cartridges.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2, or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following the invention is described in further detail with references to the drawings, wherein.

Some preferred embodiments of a bung according to the present invention will now be discussed with reference to FIG. 1, FIG. 2 and FIG. 3. Identical reference signs denote identical or comparable components.

Figure 1:
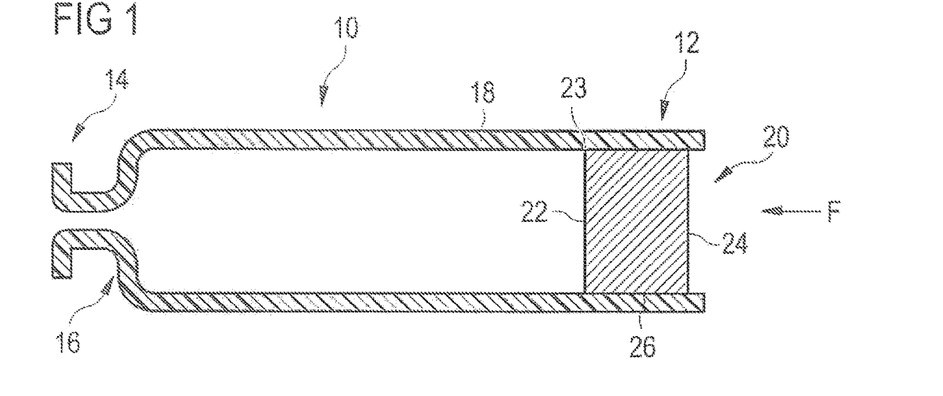
FIG. 1 shows a cross sectional view of a cartridge comprising a bung.

FIG. 1 shows a cartridge 10. The cartridge 10 comprises a distal end 14, a main body portion 18, a proximal end 12 and a narrowing shoulder portion 16. At the proximal end of the cartridge a bung 20 is shown. This bung 20 has a distal end face 22, a proximal end face 24 and a lateral area 26. The lateral area 26 of the bung 20 forms a fluid-proof sealing by contacting the main body portion 18 of the cartridge 10.

The bung 20 is moveable with respect to the cartridge 10. A piston which is not shown can apply a force F to the bung 20 and move the bung 20 towards the distal end 14 of the cartridge 10 and dispense the liquid medicinal product. While the piston is adding pressure to the bung 20, the bung 20 is compressed. This compression together with the relaxation of the bung 20 after the compression directs to an inaccuracy of the dosage dispensed from the cartridge 10, wherein dosage means a certain volume of a liquid medicinal product.

Figure 2:
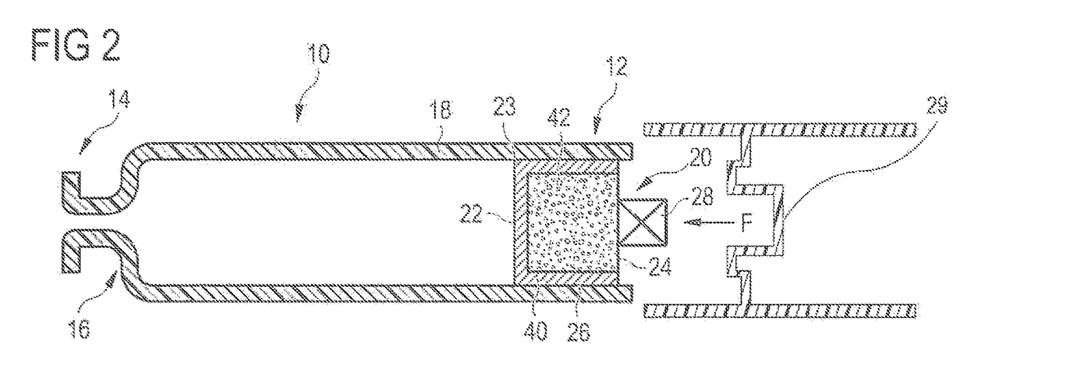
FIG. 2 shows a cross sectional view of a bung according to the present disclosure having a mechanical coding feature at the proximal end.

FIG. 2 shows a cartridge 10, wherein the bung 20 comprises two different materials and a mechanical coding feature 28 located at the proximal end face 24 of the bung 20. The bung comprises a first material 40, covering the distal end face 22 and the lateral area 26 of the bung 20. The core of the bung 20 comprises a second material 42. This second material 42 has a smaller compressibility than the first material 40.

The first material 40 seals the content of the cartridge 10 by being pressed against the inner wall of the main body portion 18. Therefore the bung forms a fluid-proof closure between the lateral area 26 of the bung 20 and the main body portion 18 of the cartridge 10. The second material 42 stabilizes the bung 20 by providing a rigid core.

The mechanical coding feature 28 is attached to the core at the proximal end of this core.

If one wants to mount the cartridge 10 according to FIG. 2 to a drug delivery device, it is necessary that the mechanical coding feature 28 at the proximal end face 24 of the bung 20 matches to the appropriate counterpart 29 in the drug delivery device. The mechanical coding feature 28 is positioned at the proximal end face 24 of the bung 20.

When a cartridge 10 is mounted to a drug delivery device and the mechanical coding feature 28 fits to the counterpart 29 in the drug delivery device the user is enabled to dispense a liquid medicinal product from the cartridge 10. After dialing a dose of the medicinal product the bung 20 is pushed towards the distal end 14 of the cartridge 10 by means of a piston, which applies a force F to the bung which is not shown in FIG. 2.

While the bung 20 is pushed towards a distal direction 14 of the cartridge 10 by means of the piston the bung 20 is compressed. Due to the low compressibility of the bung 20 caused by the properties of the second material 42 on which the force of the piston is applied, this assembly provides the bung 20 with a reduced relaxation time after compression. This leads to a reduced dripping time after injection and to a better dose accuracy.

Figure 3:
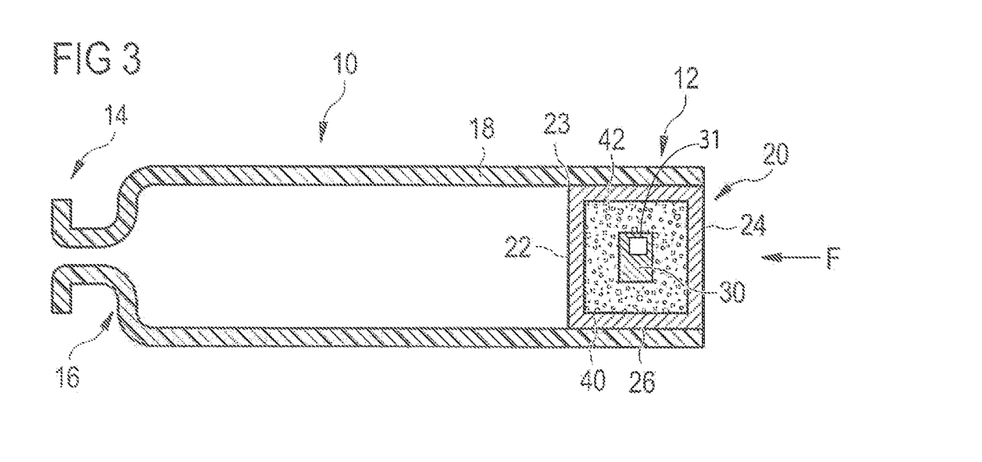
FIG. 3 shows a cross sectional view of a bung having an electronic coding feature.

FIG. 3 shows a cartridge as described in FIG. 2. The cartridge 10 comprises a bung 20 comprising two materials as mentioned in the description of FIG. 2. One difference is that the bung 20 comprises an electronic coding feature 30. Another difference is that the first material 40 covers the whole surface of the bung 20.

The electronic coding feature 30 carries information regarding the content of the cartridge and the cartridge 10 itself. The information includes the production date, the type of medicinal product that is contained and the expiry date of the content of the cartridge 10. Additional information can be stored on the electronic coding feature 30 like for example the temperature while storing, the liquid level of the cartridge 10 measured by additional sensors and transmitted to the electronic coding feature 30.

Due to the special structure comprising two different materials, the compression is limited by the layer thickness of the first material 40 at the distal end face 22 of the bung 20 and by the low compressibility of the second material 42 inside the bung 20. By having a flat surface structure at the lateral area 26 of the bung 20, the first material 40 located at the lateral area 26 is comparatively less squeezed in proximal direction while being pushed towards the narrowing shoulder portion 16 during dispensing the last dose from the cartridge 10. Thus, the dose accuracy is increased and the retention time of the bung 20 after compression is decreased.

The stored information can be read-out by means of a device that is able to interact with the electronic coding feature 30. New data regarding the content of the cartridge or the cartridge 10 can be stored on the electronic coding feature 30 at any time.

Figure 4A:
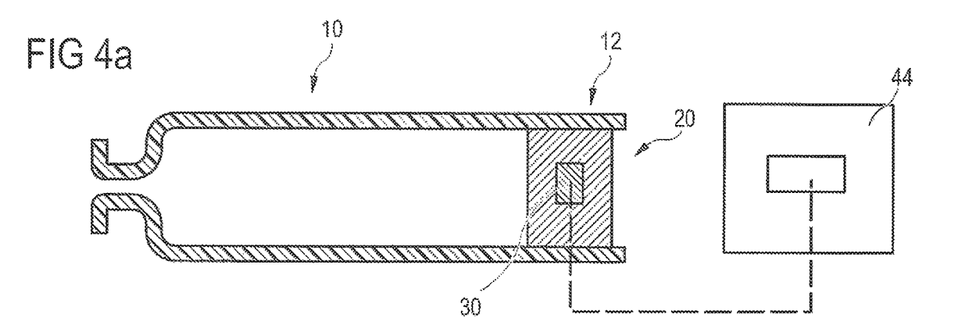
FIG. 4a shows external means which interact with an electronic coding feature which the bung of a cartridge comprises.
Figure 4B:
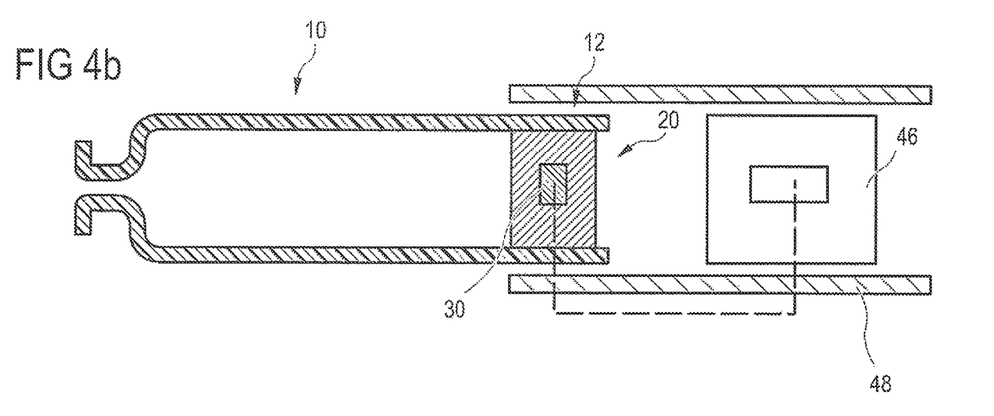
FIG. 4b shows internal means of a drug delivery device which interact with an electronic coding feature which the bung of a cartridge comprises.

FIGS. 4a and 4b show a means that is able to interact with the electronic coding feature 30.

In FIG. 4a external means 44 are shown that interact with the electronic coding feature 30 which is comprised in the bung 20 of a cartridge 10. The external means 44 enables the user to find one particular cartridge 10 which might contain one particular medicinal product within a batch of other cartridges containing another medicinal product.

In FIG. 4b an internal means 46 is shown which is able to interact with the electronic coding feature 30. The means is located inside a drug delivery device 48.

Figure 5:
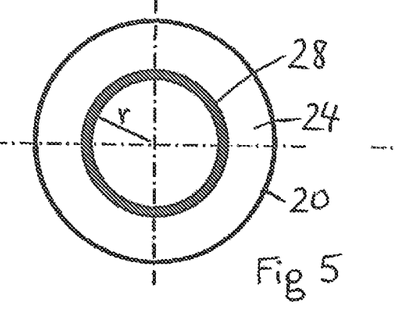
FIG. 5 shows a view onto a proximal end face of an embodiment of a bung carrying a protruding ring.

FIG. 5 shows a view onto a proximal end face 24 of an embodiment of a bung 20 carrying a protruding ring as a first mechanical coding feature 28. The protruding ring 28 has a radius r and is provided to fit into a corresponding annular trench, which is provided on the drug delivery device 48 as a second mechanical coding feature 29. A suitable cartridge 10 may be identifiable and/or distinguishable by the radius r of the protruding ring 28, which may be different for different types of cartridges 10 or different contents of cartridges 10, for example.

Figure 6:
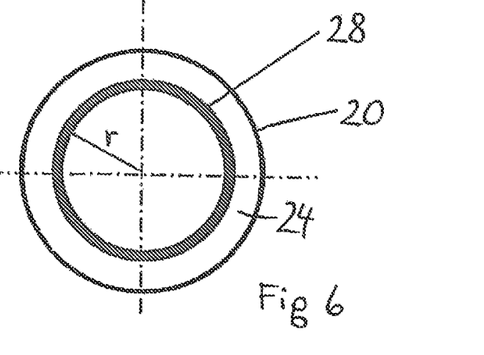
FIG. 6 shows a view onto a proximal end face of a further embodiment of a bung carrying a protruding ring.

FIG. 6 shows a view onto a proximal end face 24 of a further embodiment of a bung 20 carrying a protruding ring as a first mechanical coding feature 28. In the embodiment of FIG. 6, the protruding ring 28 has a larger radius r than the protruding ring 28 of the embodiment according to FIG. 5. The second mechanical coding feature 29 is adapted to the radius r of the protruding ring 28 and may be an annular trench having the same radius.

Figure 7:
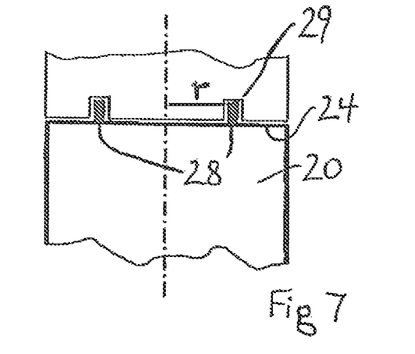
FIG. 7 shows a cross-sectional view of an arrangement of a mechanical coding feature of a bung and a counterpart of the mechanical coding feature.

FIG. 7 shows a cross-sectional view of an arrangement of a protruding ring of radius r provided as a first mechanical coding feature 28 of a bung 20 and a second mechanical coding feature 29 provided on the drug delivery device 48 as a counterpart of the first mechanical coding feature 28. The FIG. 7 shows that the protruding ring 28, which is applied to the proximal end face 24 of the bung 20, fits into a corresponding annular trench forming the second mechanical coding feature 29 of the drug delivery device 48.

Figure 8:
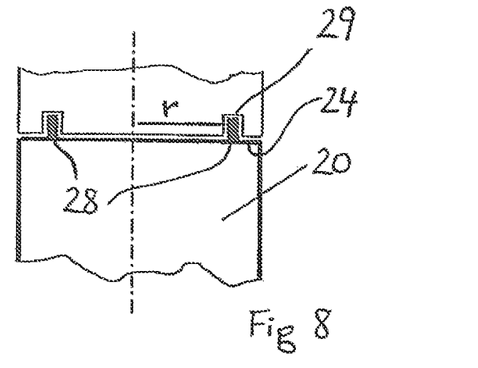
FIG. 8 shows a cross-sectional view of an arrangement of a further embodiment of a mechanical coding feature of a bung and a counterpart of the further mechanical coding feature.

FIG. 8 shows a cross sectional view of an arrangement of a further embodiment of a protruding ring provided as a first mechanical coding feature 28 of a bung 20 and a second mechanical coding feature 29 provided on the drug delivery device 48 as a counterpart of the further first mechanical coding feature 28. The protruding ring 28 is applied to the proximal end face 24 of the bung 20 and fits into a corresponding annular trench forming the second mechanical coding feature 29 of the drug delivery device 48. The protruding ring 28 of the embodiment according to FIG. 8 and the corresponding trench have a larger radius r than the protruding ring 28 of the embodiment according to FIG. 7.

Figure 9:
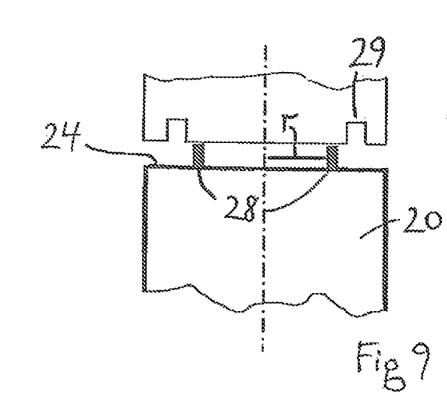
FIG. 9 shows a cross-sectional view of an arrangement of a mechanical coding feature of a bung according to FIG. 7 and a counterpart of a mechanical coding feature according to FIG. 8.

FIG. 9 shows a cross-sectional view of an arrangement of a first mechanical coding feature 28 of a bung 20 according to FIG. 7 and a second mechanical coding feature 29 provided as a counterpart of a first mechanical coding feature according to FIG. 8.

The first mechanical coding feature 28 is a protruding ring of radius r, and the second mechanical coding feature 29 is a trench of larger radius. The FIG. 9 shows that the first mechanical coding feature 28 and the second mechanical coding feature 29 do not fit in this arrangement, and hence a selection of the cartridge 10 is facilitated.

Figure 10:
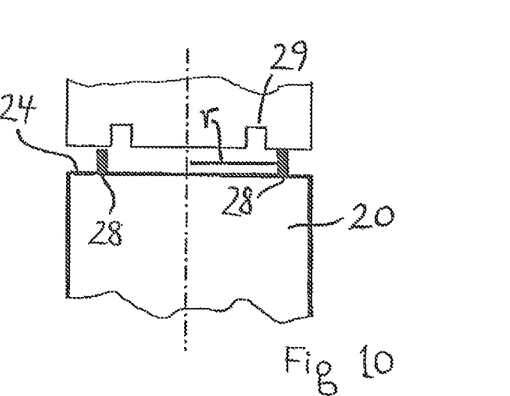
FIG. 10 shows a cross-sectional view of an arrangement of a mechanical coding feature of a bung according to FIG. 8 and a counterpart of a mechanical coding feature according to FIG. 7.

FIG. 10 shows a cross-sectional view of an arrangement of a first mechanical coding feature 28 of a bung 20 according to FIG. 8 and a second mechanical coding feature 29 provided as a counterpart of a first mechanical coding feature according to FIG. 7. The first mechanical coding feature 28 is a protruding ring of radius r, and the second mechanical coding feature 29 is a trench of smaller radius. The FIG. 10 also shows that the first mechanical coding feature 28 and the second mechanical coding feature 29 do not fit in this arrangement, and hence a selection of the cartridge 10 is facilitated.

Figure 11:
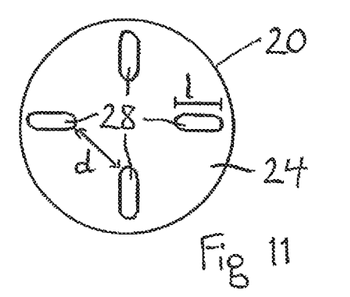
FIG. 11 shows a view onto a proximal end face of an embodiment of a bung carrying a plurality of relief structures.

FIG. 11 shows a view onto a proximal end face 24 of an embodiment of a bung 20 carrying a plurality of relief structures provided as a first mechanical coding feature 28. In this embodiment the relief structures are similar to one another and have an elongated shape, so that a length l of the relief structures can be defined by a maximal dimension of a relief structure measured in the plane of the proximal end face 24. The relief structures may be disposed on a circle, for example, as shown in FIG. 11, and in this embodiment the relief structures are arranged parallel to a radius of the circle. This means that the length l is measured in the direction of a radius of the circular proximal end face 24. The relief structures are arranged at a minimal distance d from one another. In the embodiment of FIG. 11, the minimal distance d is the same for each pair of neighboring relief structures.

Figure 12:
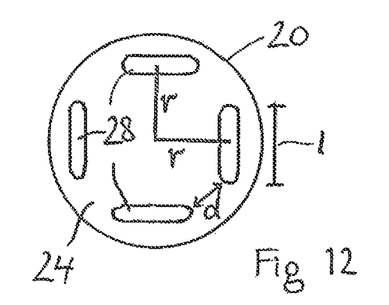
FIG. 12 shows a view onto a proximal end face of a further embodiment of a bung carrying a plurality of relief structures.

FIG. 12 shows a view onto a proximal end face 24 of a further embodiment of a bung 20 carrying a plurality of relief structures provided as a first mechanical coding feature 28. In this embodiment the relief structures are similar to one another and have an elongated shape, so that a length l of the relief structures can be defined by a maximal dimension of a relief structure measured in the plane of the proximal end face 24. In this embodiment the length l is larger than the length of the relief structures of the embodiment according to FIG. 11. In the embodiment according to FIG. 12, the relief structures are arranged on a circle, and each relief structure is arranged transverse to a radius of the circle.

In further embodiments the relief structures may have different lengths and/or different directions and/or different minimal distances from one another. The relief structures need not be arranged on a circle, although a rotationally symmetric arrangement of the relief structures may be preferred. The relief structures need not have the same shape. They may be statistically dispersed on the proximal end face 24, although a regular arrangement of similar relief structures may be preferred to facilitate the formation of the corresponding second mechanical coding features 29 of the drug delivery device 48.

Figure 13:
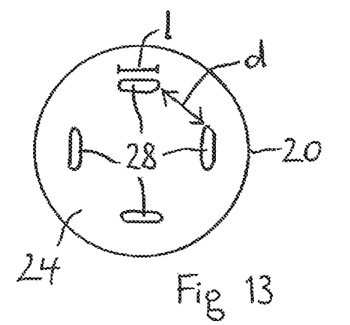
FIG. 13 shows a view onto a proximal end face of a further embodiment of a bung carrying a plurality of relief structures.

FIG. 13 shows a view onto a proximal end face 24 of a further embodiment of a bung 20 carrying a plurality of relief structures provided as a first mechanical coding feature 28. Compared to the embodiment of FIG. 12, the embodiment of FIG. 13 comprises relief structures of smaller length l, which are arranged on a circle of smaller radius and at a larger minimal distance d from one another.

Figure 14:
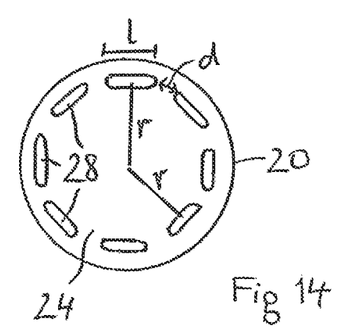
FIG. 14 shows a view onto a proximal end face of a further embodiment of a bung carrying a plurality of relief structures.

FIG. 14 shows an arrangement of a larger number of relief structures on a circle and transverse to a radius of the circle. The length l and the minimal distance d are again different from the corresponding dimensions of the previously described embodiments. FIGS. 12 to 14 show how a plurality of relief structures can be designed according to the same basic pattern, which allows for sufficient differences to enable an identification of different cartridges 10. The bungs 20 can thus be provided with different mechanical coding features in essentially the same manufacturing process.

The first mechanical coding feature 28 of the bung 20 may especially be a separator, which is also provided to facilitate a separation of the bungs during a bulk storage. The separators are protruding structures on the surface of a bung and prevent the bungs from adhering to one another when they are stored together in a bulk.

REFERENCE NUMERALS 10 cartridge
12 proximal end of the cartridge
14 distal end of the cartridge
16 shoulder portion
18 main body portion
20 bung
22 distal end face
23 edge of the distal end face
24 proximal end face
26 lateral area
28 mechanical coding feature
29 counterpart of the mechanical coding feature
30 electronic coding feature
40 first material
42 second material
44 external means
46 internal means
48 drug delivery device
d minimal distance
F force
l length
r radius

The invention claimed is:

1. A cartridge for containing a medicinal product, the cartridge comprising:
    (a) a main body; and
    (b) a bung moveable along a longitudinal axis of the cartridge, the bung comprising an electronic coding feature for carrying information regarding the cartridge, the content of the cartridge, or both, wherein the electronic coding feature is fully encased within the bung of the cartridge for containing the medicinal product, wherein the electronic coding feature comprises a transponder, an integrated circuit, an RFID member, a solid state memory, or any combination of the aforementioned, wherein the bung further comprises a first material in a first region of the bung covering at least the whole lateral area of the bung and a second material in a second region of the bung different than the first region of the bung and at least partially arranged inside the bung, the second material having a smaller compressibility than a compressibility of the first material, and wherein the second material surrounds the electronic coding feature on all sides and the first material surrounds the electronic coding feature on all sides.

2. The cartridge according to claim 1, wherein the electronic coding feature comprises a transponder.

3. The cartridge according to claim 2, wherein the transponder is a radio-frequency identification (RFID)-member.

4. The cartridge according to claim 2, wherein the transponder is a passive transponder.

5. The cartridge according to claim 2, wherein the transponder is an active transponder.

6. The cartridge according to claim 5, wherein the active transponder comprises one or more integrated sensors.

7. The cartridge according to claim 1, wherein the electronic coding feature is surrounded on all sides by an electrically isolating material.

8. The cartridge according to claim 1, wherein the electronic coding feature is surrounded on all sides by a polymer-matrix.

9. The cartridge according to claim 1, wherein the first material covers the whole outer surface of the bung.

10. The cartridge according to claim 1, wherein the first material comprises a first polymer and the second material comprises a second polymer.

11. The cartridge according to claim 1, wherein the cartridge contains a medicinal product.

12. The cartridge according to claim 1, wherein the electronic coding feature is located proximal to the center of the bung.

13. A drug delivery device comprising:
a cartridge according to claim 1; and
a piston configured to apply a force to the bung.

14. The drug delivery device according to claim 13, wherein the drug delivery device is configured to interact with the electronic coding feature.

15. The drug delivery device according to claim 14, wherein the drug delivery device comprises an electromagnetic sensing device configured to interact with the electronic coding feature.

16. A system comprising:
a drug delivery device according to claim 13; and
an external sensing device arranged outside of the drug delivery device, the external sensing device comprising a sensor, wherein the external sensing device is configured to interact with the electronic coding feature.

17. The system according to claim 16, wherein the external sensing device is an electromagnetic sensing device.

18. The system of claim 16, wherein the sensor is an RFID reader.

19. A method of identifying a cartridge according to claim 1, wherein the cartridge contains a medicinal product and the bung is located inside the cartridge, wherein the electronic coding feature is carrying information regarding the cartridge, the content of the cartridge, or both, and wherein the method comprises:
obtaining at least some of the information from the electronic coding feature; and
using the obtained information to distinguish the cartridge and the content of the cartridge within a batch of other cartridges.

20. A method of manufacturing a cartridge according to claim 1, wherein the bung is manufactured by injection molding.

21. A method of manufacturing a cartridge according to claim 10, wherein the method of manufacturing the bung comprises the steps of:
(i) forming a shell comprising the first material by injection molding;
(ii) adding monomers and the electronic coding feature inside the shell; and
(iii) polymerizing the monomers to form the second material.

* * * * *